United States Patent [19]

Wolfinger

[11] 4,080,342

[45] Mar. 21, 1978

[54] N-(α-ALKYLBENZYLTHIO)SUCCINIMIDE

[75] Inventor: Mark D. Wolfinger, Akron, Ohio

[73] Assignee: Monsanto Company, St. Louis, Mo.

[21] Appl. No.: 747,710

[22] Filed: Dec. 6, 1976

[51] Int. Cl.² ............................................. C07D 207/48
[52] U.S. Cl. ........................... 260/326.5 S; 260/79.5 R; 260/784
[58] Field of Search ...................... 260/326.5 S, 79.5 R

[56] References Cited

U.S. PATENT DOCUMENTS 3,752,824  8/1973  Coran et al. .................... 260/326.5 S Primary Examiner—Donald G. Daus
Assistant Examiner—Jose Tovar

[57] ABSTRACT

Compounds of the formula

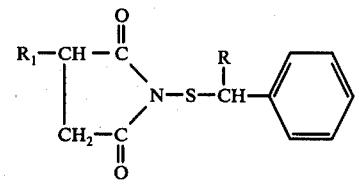

in which R and $R_1$ are alkyl are described which compounds are potent inhibitors of premature vulcanization of rubber.

3 Claims, No Drawings

N-(α-ALKYLBENZYLTHIO)SUCCINIMIDE

This invention relates to an improved process for inhibiting premature vulcanization of rubber and to compounds which are especially potent premature vulcanization inhibitors.

BACKGROUND OF THE INVENTION

The use of sulfur derivatives of amido compounds to inhibit the premature vulcanization of vulcanizable rubber compositions is known. For example, see Coran and Kerwood, U.S. Pat. No. 3,546,185.

SUMMARY OF THE INVENTION

It has been discovered that α-alkyl substituted-benzylthio derivatives of succinimide are especially potent premature vulcanization inhibitors. Surprisingly, the presence of an alkyl substituent on the alpha carbon of benzyl enhances the prevulcanization inhibitor activity. The improved inhibitors of the invention are characterized by the formula

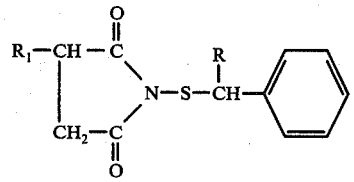

in which R is lower alkyl of 1-5 carbon atoms, preferably, R is methyl or ethyl and $R_1$ is hydrogen or alkyl of 1-10 carbon atoms.

Compounds of the invention may be prepared by reacting the appropriate sulfenyl chloride with succinimide or alkylsuccinimide in the presence of a hydrogen chloride acceptor. Alternatively, the sulfenyl chloride may be reacted with an alkali metal salt of succinimide. Another procedure comprises reacting a N-halo succinimide with a 1-phenylalkanethiol such as 1-phenylethanethiol or 1-phenylpropanethiol.

Illustrative examples of compounds of the invention are:
N-(α-methylbenzylthio)succinimide
N-(α-ethylbenzylthio)succinimide
N-(α-propylbenzylthio)succinimide
N-(α-butylbenzylthio)succinimide
N-(α-pentylbenzylthio)succinimide
N-(α-methylbenzylthio)methylsuccinimide
N-(α-ethylbenzylthio)methylsuccinimide
N-(α-propylbenzylthio)methylsuccinimide
N-(α-methylbenzylthio)-n-dodecylsuccinimide
N-(α-ethylbenzylthio)-n-dodecylsuccinimide The inhibitors of the invention are incorporated into rubber stocks by mixing on a mill or in an internal mixer such as a Banbury mixer. However, the inhibitors may be incorporated by addition to latex, if desired. The process of the invention is particularly applicable to sulfur-vulcanizable rubber compositions which rubber compositions contain a sulfur vulcanizing agent such as an amine disulfide or a polymeric polysulfide but preferably, the vulcanizing agent is elemental sulfur. Rubber compositions containing organic accelerating agents are particularly improved by the inhibitors of the invention. Any organic accelerating agents which accelerate the sulfur vulcanization of rubber is satisfactory in the practice of this invention. Examples of suitable accelerators are described in U.S. Pat. No. 3,546,185, col. 9, lines 53-75 and in U.S. Pat. No. 3,780,001, col. 4, lines 43-72. The process of the invention is applicable to a wide variety of natural and synthetic rubbers and mixtures thereof. Examples of satisfactory rubbers are described in U.S. Pat. No. 3,546,185, col. 10, lines 15-21 and U.S. Pat. No. 3,780,001, col. 5, lines 5-33. The vulcanizable composition may also contain conventional compounding ingredients such as reinforcing pigments, extenders, processing oils, antidegradants and the like.

Small amounts of inhibitors are effective to inhibit premature vulcanization. Improvements in processing safety may be observed with 0.05 parts or less of inhibitor per 100 parts rubber. Although there is no upper limit in the amount of inhibitor used, generally the amount does not exceed 5 parts inhibitor per 100 parts rubber. Typically, the amount of inhibitor added is about 0.1 to 2.5 parts per 100 parts rubber with amounts of about 0.2 to 1 parts inhibitor per 100 parts rubber being commonly used. Methods for determining scorch times and curing characteristics of rubber stock which methods were also used in demonstrating this invention are described in U.S. Pat. No. 3,546,185, col. 13, lines 30-53.

DESCRIPTION OF PREFERRED EMBODIMENTS

Example 1

To a suitable reactor equipped with temperature controlling means and stirring means, there are charged, while maintaining the temperature at about room temperature, N-chlorosuccinimide (about 0.30 mole) in 400 ml of benzene and 1-phenylethanethiol (about 0.30 mole) in 50 ml of benzene. After stirring the reaction mixture 10 minutes, triethylamine (0.32 mole) in 50 ml of benzene is added dropwise. The benzene mixture is stirred one hour and then filtered. The filtrate is washed three times with 250 ml portions of water and then subjected to vacuum with heating to strip off volatile components. A crystalline residue is recrystallized from ethanol to give 26 grams of N-(α-methylbenzylthio)succinimide, m.p. 121-125° C.

The process of the invention is demonstrated by using the following natural rubber and synthetic rubber masterbatches.

|  | Masterbatches | |
|---|---|---|
|  | NR | SBR |
| Smoked sheets | 100 | — |
| Oil-extended styrene-butadiene rubber 1712 | — | 137.5 |
| ISAF carbon black | 45 | 65 |
| Zinc oxide | 3 | 3 |
| Stearic acid | 2 | 1 |
| Processing oil | 5 | 1.5 |
| Sulfur | 2 | 2 |
| N-(1,3-dimethylbutyl)-N'-(phenyl)-p-phenylenediamine | 2 | 2 |
| N-(tert-butyl)-2-benzothiazole-sulfenamide | 0.5 | 0.5 |
|  | 159.5 | 212.5 |

Portions of the masterbatches containing no inhibitors are controls, stocks 1 and 4. A quantity of N-(benzylthio)-succinimide, a known inhibitor, is incorporated into other portions of the masterbatches, stocks 2 and 4, and a like quantity of N-(α-methylbenzylthio)succinimide, an inhibitor of the invention, is incorporated into still other portions of the masterbatches, stocks 3 and 6.

The properties of the vulcanizable compositions are measured by conventional methods as described above. The results are shown in Table I.

TABLE I

| Stock Number | 1 | 2 | 3 | 4 | 5 | 6 |
|---|---|---|---|---|---|---|
| NR-Masterbatch | 159.5 | 159.5 | 159.5 | — | — | — |
| SBR-Masterbatch | — | — | — | 212.5 | 212.5 | 212.5 |
| N-(benzylthio)succinimide | — | 0.5 | — | — | 0.5 | — |
| N-(α-methylbenzylthio)succinimide | — | — | 0.5 | — | — | 0.5 |
| Mooney scorch | 121° C | 121° C | 121° C | 135° C | 135° C | 135° C |
| $t_5$, minutes | 33.9 | 43.2 | 75.0 | 26.0 | 30.0 | 44.0 |
| % increase in scorch delay | — | 27 | 121 | — | 15 | 69 |
| Rheometer data | 144° C | 144° C | 144° C | 153° C | 153° C | 153° C |
| $t_2$ | 8.8 | 10.8 | 15.0 | 10.3 | 11.2 | 15.5 |
| $t_{90}$-$t_2$ | 12.0 | 13.0 | 15.1 | 20.2 | 19.0 | 20.7 |
| R max | 65.3 | 67.4 | 66.2 | 56.7 | 56.0 | 54.9 |
| Stress - Strain data | 144° C | 144° C | 144° C | 153° C | 153° C | 153° C |
| 300% modulus. Kg./sq.cm. | 120 | 118 | 115 | 88 | 84 | 81 |
| Ult. tensile strength, Kg./sq.cm. | 280 | 263 | 255 | 193 | 205 | 203 |
| % Ult. elongation | 540 | 530 | 520 | 610 | 600 | 600 |

The data show that N-(α-methylbenzylthio)succinimide is about four times more potent as a prevulcanization inhibitor than N-(benzylthio)succinimide. The inhibitor of the invention increases the scorch delay 121% in the NR stock and 69% in the SBR stock compared with only a 27% increase in scorch delay in the NR stock and 15% increase in scorch delay in the SBR stock for the known inhibitor. Similar improved results are obtained with other inhibitors of the invention. Compounds of the invention wherein $R_1$ is hydrogen are more potent inhibitors than compounds wherein $R_1$ is alkyl, however, vulcanizates containing compounds of the invention wherein $R_1$ is alkyl, particularly alkyl of 6-10 carbon atoms, exhibit less surface blooming than compounds wherein $R_1$ is hydrogen.

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property or privilege is claimed are defined as follows:

1. A compound of the formula

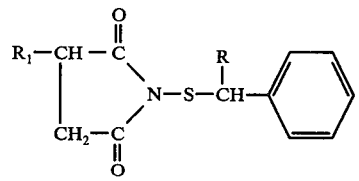

in which R is lower alkyl and $R_1$ is hydrogen or alkyl of 1-10 carbon atoms.

2. The compound of claim 1 in which $R_1$ is hydrogen.

3. The compound of claim 2 in which R is methyl.

* * * * *